(12) United States Patent
Larkins

(10) Patent No.: US 8,841,348 B2
(45) Date of Patent: Sep. 23, 2014

(54) ANTI-INFLAMMATORY FORMULATION

(75) Inventor: Nicholas John Larkins, London (GB)

(73) Assignee: AKL Inflammatory Limited, St. Martins (GB)

( * ) Notice: Subject to any disclaimer, the term of this patent is extended or adjusted under 35 U.S.C. 154(b) by 1292 days.

(21) Appl. No.: 11/918,185

(22) PCT Filed: Apr. 7, 2006

(86) PCT No.: PCT/GB2006/001279
§ 371 (c)(1),
(2), (4) Date: Feb. 17, 2009

(87) PCT Pub. No.: WO2006/106350
PCT Pub. Date: Oct. 12, 2006

(65) Prior Publication Data
US 2009/0215886 A1    Aug. 27, 2009

(30) Foreign Application Priority Data
Apr. 8, 2005    (GB) .................................. 0507208.7

(51) Int. Cl.
| | | |
|---|---|---|
| *A61K 31/12* | (2006.01) | |
| *A61K 31/05* | (2006.01) | |
| *A01N 31/08* | (2006.01) | |
| *A01N 35/00* | (2006.01) | |
| *A61K 36/65* | (2006.01) | |
| *A61K 31/216* | (2006.01) | |

(52) U.S. Cl.
CPC ............... *A61K 31/216* (2013.01); *A61K 36/65* (2013.01); *A61K 31/12* (2013.01)
USPC ........... 514/688; 514/731; 514/576; 514/689; 514/734

(58) Field of Classification Search
USPC .......................... 514/183; 424/725, 773, 775
See application file for complete search history.

(56) References Cited

U.S. PATENT DOCUMENTS

| | | | |
|---|---|---|---|
| 6,280,751 B1 * | 8/2001 | Fletcher et al. ................ | 424/401 |
| 6,733,800 B1 * | 5/2004 | Rajgarhia ...................... | 424/757 |
| 2004/0022879 A1 * | 2/2004 | Larkins .......................... | 424/752 |

OTHER PUBLICATIONS

Chou, "Anti-inflammatory and analgesic effects of paeonol in carrageenan-evoked thermal hyperalgesia", Br.J.Pharmacology, 2003, vol. 139, No. 6, pp. 1146-1152.*
Lin et al. "Aggregation Inhibitory Activity of Minor Acetophenones from *Paeonia* Species", Planta Medica, 1999, vol. 65, pp. 595-599.*
Barbieri et al. "Apocynin prevents cyclooxygenase 2 expression in human monocytes through NADPH oxidase and glutathione redox-dependent mechanisms", FreeRad.Bio.Med., 2004, vol. 37, No. 2, pp. 156-165.*

* cited by examiner

*Primary Examiner* — James D Anderson
*Assistant Examiner* — Stephanie Springer
(74) *Attorney, Agent, or Firm* — Flynn, Thiel, Boutell & Tanis, P.C.

(57) ABSTRACT

Compositions containing apocynin and paeonol. The compositions may be used for the treatment of inflammatory diseases.

12 Claims, No Drawings

ANTI-INFLAMMATORY FORMULATION

The present invention relates to anti-inflammatory and/or analgesic formulations for the treatment of humans or animals.

The use of NSAIDs, non-steroidal anti-inflammatory drugs, for pain relief is well known. However, treatment with such drugs can result in undesirable side-effects (e.g. gastrointestinal tract (GIT) related problems such as nausea, gastric reflux, gastric ulceration and constipation). Further, there are an increasing number of people who are not able to use conventional pharmaceuticals (for example, due to allergies, side-effects or for ethical reasons). The use of corticosteroid anti-inflammatory drugs is well established—however their undesirable side-effects are numerous and include immunosupression, fluid retention and weight gain. There is therefore a need for an improved non-conventional anti-inflammatory formulation. There is also a need, for formulations which do not cause GIT problems.

According to the present invention there is provided a composition, e.g. a pharmaceutical preparation, comprising apocynin and paeonol.

Apocynin is a plant phenol, 4-hydroxy-3-methoxyacetophenone, and has the following formula:

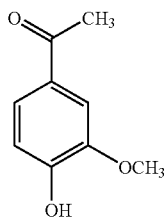

Apocynin is found in plant substances and plant extracts, for example in extracts of the plants *Picrorrhiza kurroa, Apocynum cannabinium, Apocynum venatum, Apocynum androsaemifolium* and vanilla species such as *Vanilla planifolia*.

The compositions and preparations of the invention may include "isolated" apocynin. Isolated apocynin is apocynin which has been synthesised, or which has been extracted from plants and purified. Alternatively or additionally, apocynin may be present in compositions or preparations according to the invention as direct extracts from plants such as those mentioned above (for example as part of an unresolved mixture of compounds in the form of an unpurified plant or root extract). These will be referred to as apocynin "in the natural form" or "natural apocynin". For example, apocynin present in preparations according to the invention in the form of *Picrorrhiza kurroa* will be referred to as "natural apocynin". The term "natural apocynin" or apocynin "in the natural form" also includes glycosides of apocynin such as those found in the plant species in which apocynin is found. Such glycosides include androsin and other iridoid glycosides, for example. Preferably, the composition includes apocynin in a purified or synthetic form: "isolated" apocynin.

The composition may include apocynin as part of an unresolved mixture of compounds in the form of an unpurified plant or root extract: "natural" apocynin. The use of the active entity in the natural form in combination with the isolated active apocynin may lead to a synergistic effect between the isolated form (e.g. purified or synthetic apocynin) and the natural form (e.g. apocynin included in *Picrorrhiza kurroa*). The preferred *Picrorrhiza kurroa* is an extract in a standardised form based on a standardised iridoid glucoside fraction, such forms are well known. A preferred *Picrorrhiza kurroa* extract in standardised form comprises *Picrorrhiza kurroa* standardised to "Kutkin min. 4%". Standardised iridoid glucoside fractions between Kutkin min. 2% and Kutkin min. 8% are also preferred. In the Examples below, the *Picrorrhiza kurroa* extract in standardised form comprises standardised iridoid glucoside fractions collectively known as "Kutkin min. 2%". Kutkin is obtained by crystallization and consists of the glucosides picroside I and kutoside in a ratio of 1:2 and other minor glycoside (Sing and Rastogi, 1972, Ansari et al., 1988).

As indicated above, the composition may include apocynin which is in the natural form only, for example, *Picrorrhiza kurroa*. However, if this is the case, it may be necessary to limit the amount of *Picrorrhiza kurroa* to prevent side effects (such as stomach upsets which may occur due to other phytochemical species in the *Picrorrhiza kurroa*). However, it is noted that most human subjects can take up to 2,000 mg of *Picrorrhiza kurroa* (Kutkin min. 2%) per day without discomfort.

Paeonol is 2-hydroxy-4-methoxy-acetophenone and is shown by the following formula:

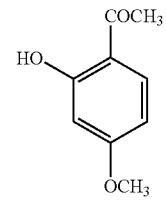 [SMILES: COc1ccc(C(C)=O)c(O)c1]

It may be found in plant substances and plant extracts.

For example paeonol may be found in *Paeonia suffruticosa, Paeonia lactiflora, Paeonia veitchii, Paeoniaobovata, Glycyrrhiza glabra, -Cynanchum panniculatum, Rheum palmatum* (rhizome) and *Scutellaria baicalensis* (root).

The compositions and preparations of the invention may include "isolated" paeonol, that is paeonol which has been synthesised or paeonol which has been extracted from plants and purified. Paeonol may be present in preparations according to the invention as direct extracts from plants (i.e. as part of an unresolved mixture of compounds in the form of an unpurified plant or root extract). These will be referred to a paeonol "in the natural form" or "natural paeonol". For example, paeonol present in preparations according to the invention in the form of *Paeonia suffruticosa* will be referred to as "natural paeonol". The terms paeonol "in the natural form" or "natural paeonol" include glycosides of paeonol such as those found in the plant species in which paeonol is found. Such glycosides include paeonin, paeonolide and paeonoside, for example.

Preferably the composition includes paeonol in a purified or synthetic form: "isolated" paeonol.

Alternatively or additionally the paeonol may be present in natural form.

Preferably, the composition according to the invention further comprises L-glutamine.

Preferably the composition according to the invention further comprises a filler. Preferred fillers include at least one flavonoid, preferably a mixture of one or more flavonoids.

Preferred compositions further comprise glucosamine.

A preferred composition comprises apocynin and paeonol wherein the ratio (by weight) of apocynin to paeonol is between about 1 to 100 and about 100 to 1, preferably between about 1 to 10 and 1 to 30, more preferably between about 1 to 1 and 1 to 20, more preferably between about 1 to 2 and 1 to 10.

A preferred composition includes isolated apocynin and isolated paeonol and the ratio (by weight) of isolated apocynin to isolated paeonol is between 1:1 and 1:10, more preferably between 1:2 and 1:6, more preferably between 1:3 and 1:6, more preferably between 1:3 and 1:5, more preferably between 1:3 and 1:4. The composition may also include natural apocynin and/or natural paeonol.

In the ratios above, the weights of apocynin and paeonol refer to the weight of the components in the isolated form (e.g. isolated apocynin and isolated paeonol).

A preferred composition comprises apocynin and paeonol wherein apocynin is present in isolated form and in the natural form (e.g. *Picrorrhiza kurroa*). Preferably, the ratio (by weight) of isolated apocynin to apocynin in the natural form is between about 10 to 1 and 1 to 1 (based on a calculation where the natural apocynin is in the form of *Picrorrhiza kurroa* standardised to Kutkin min. 2%).

A further preferred composition comprises apocynin and paeonol wherein apocynin is present in the isolated form and paeonol is present in the isolated form and in the natural form (e.g. *Paeonia suffruticosa*). Preferably the ratio (by weight) of isolated paeonol to paeonol in the natural form is between about 10 to 1 and 0.1 to 1, more preferably between 4:1 and 2:1 (based on a calculation where the natural paeonol is in the form of *Paeonia suffruticosa* as Moutan cortex).

A preferred composition comprises apocynin and paeonol wherein apocynin is present in isolated form and in the natural form (e.g. *Picrorrhiza kurroa*); and paeonol is present in isolated form and in the natural form (e.g. *Paeonia suffruticosa* or *Glycyrrhiza glabra*).

Preferably the composition includes one or both of paeonol and apocynin in isolated form.

If the composition includes apocynin which is only in the natural form (that is no isolated apocynin) and paeonol which is only in the natural form (that is no isolated paeonol), it is preferred that the % by weight of the total composition which is apocynin in the natural form (e.g. *Picrorrhiza kurroa*) is at least 2.5% (more preferably at least 5%); and/or the % by weight of the total composition which is paeonol in the natural form (e.g. *Paeonia suffruticosa* or *Glycyrrhiza glabra*) is at least 2.5% (more preferably at least 5%).

It is preferred that if the composition includes apocynin which is only in the natural form (e.g. *Picrorrhiza kurroa*) and paeonol which is only in the natural form (in other words, if the composition according to the invention includes no isolated apocynin and no isolated paeonol), the paeonol in the natural form is not in the form of *Glycyrrhiza glabra*. If the composition includes apocynin which is only in the natural form which is *Picrorrhiza kurroa* and paeonol which is only in the natural form (in other words, if the composition according to the invention includes no isolated apocynin and no isolated paeonol), and the paeonol is in the form of *Glycyrrhiza glabra*, it is preferred that the ratio of *Glycyrrhiza glabra* and *Picrorrhiza kurroa* is not between 2:1 and 1:3 by weight.

Preferred compositions further comprise L-glutamine at a ratio (by weight of apocynin to L-glutamine) of between 1 to 10 and 1 to 40, more preferably between about 1 to 15 and 1 to 25.

Preferred compositions further comprise glucosamine at a ratio (by weight of apocynin to glucosamine) of between 1 to 10 and 1 to 40, more preferably between about 1 to 15 and 1 to 25.

Preferably the composition further includes a binder.

The compositions may be used as pharmaceutical preparations, for the treatment of disease in humans, or veterinary preparations, for the treatment of non-human animals.

The preparations (or compositions) may further comprise additional components such as pharmaceutically conventional carriers, diluents, flavourings, emulsifiers and stabilisers. They may comprise additional components (for example carriers or diluents) which are "conventional" in herbal remedies. Preferably the pharmaceutical or veterinary preparation (or composition) further comprises one or more of the following:

[1] an agent to enhance the immune system, for example lactoferrin which has antiviral antibacterial and antioxidant effects;
[2] a natural source of vitamins such as bee pollen;
[3] a source, for example a natural source, of vitamins, minerals and amino acids, for example *chlorella*;
[4] a source of trace elements, for example chromium and/or vanadium and/or copper and/or zinc and/or manganese
[5] taste-masking agents, for example yoghurt, fruit juice, honey and syrup.

The compositions and pharmaceutical/veterinary preparations are suitable for oral administration. The methods of formulation of the compositions for oral administration are well known in the art. For example, the composition for administration may be prepared using a pharmaceutically acceptable carrier in a form suitable for administration. Such a carrier can be prepared as a tablet, a pill, a sugar-coated agent, a capsule, a liquid, a gel, a syrup, a slurry, a suspension, etc. The carrier may be a herbal binder such as *Glycyrrhiza glabra* or one or more pharmaceutically acceptable carriers such as liposomes, lactose, trehalose, sucrose, mannitol, xylitol, crystalline cellulose, chitosan, calcium carbonate, talc, titanium oxide, or silica (silicon oxide) or the like.

The composition may be obtained, for example, by combining the active ingredients with a solid excipient, pulverizing the mixture (if necessary) and inserting into a capsule, for example, a soft sealed capsule consisting of a gelatin capsule, gelatin and coating (e.g., glycerol or sorbitol) or a capsule composition suitable for vegetarians. In the soft capsule, the composition may be dissolved or suspended in an appropriate liquid, such as a fatty oil, liquid paraffin or liquid polyethylene glycol, with or without a stabilizer.

The formulation (composition or preparation) may also be in the form of a standardised liquid extract. Standardised liquid extracts may in some circumstances have advantages when compared to the solid dose forms (tablets and hard shell capsules). They may involve minimal processing during manufacture and may reflect the true spectrum of the original herb (or plant etc.), in a compact and convenient form. There is also the possibility of superior bioavailability as the preparation is already in the liquid form. The prescribed dose may then be easily diluted (water, fruit juice, adding ice etc.) so as to minimise the experience of any unpleasant taste, thus increasing the likelihood of patient compliance.

It will be appreciated that the preparations are suitable for other means of administration, for example mucosal delivery routes (for example rectal, nasal, vaginal) and also topical administration. The methods of formulation of the compositions for use in these methods are well known in the art.

The compositions and preparations may be used as (or in the manufacture of) pharmaceuticals for human subjects. They may also be used as (or in the manufacture of) veterinary preparations to non-human animals, for example dogs, cats, pigs, equine species, poultry and reared game birds such as pheasants.

The preparations are particularly suited to the treatment of inflammatory diseases, in particular inflammatory joint disease.

According to the present invention in a further aspect, there is provided the use of apocynin and paeonol in (or in the manufacture of) a preparation for the treatment of inflammatory disease.

The inflammatory diseases may be an inflammatory disease such as in inflammatory joint disease, arthritis and rheumatoid osteoarthritis, dermatitis, (atopic) dermatitis, sinusitis, hay-fever syndrome (allergic rhinitis, allergic lung diseases, inflammatory diseases of the gastro-intestinal tract, such as ulcers) including stomach ulcers), ulcerative colitis, gastric ulcer syndrome, celiac disease, irritable bowel syndrome, irritable bowel disease and Crohn's disease. They may be used to treat inflammatory diseases such as seasonal pruritic dermatitis, laminitis, eczematous dermatitis, COPD, lameness, azoturia, dermatitis, osteoarthritis, hip dysplasia and equine gastro ulcer syndrome of the sequellae thereof. The inflammatory disease may also be the treatment of inflammation or swelling, following, for example, injury or surgery (e.g. following an operation such as a hip replacement). The treatment of inflammatory disease may include treatment of joint swelling.

Preferably the preparation (or composition) is administered to a subject (human or animal) at a concentration, per daily dose, of apocynin, of between 1 mg/kg body weight and 50 mg/kg body weight, more preferably 5 to 8 mg/kg body weight. Preferably, the preparation is administered to a human or animal subject at a concentration, per daily dose, of paeonol of 5 mg/kg body weight to 70 mg/kg body weight, more preferably between about 10 mg/kg and 45 mg/kg body weight, more preferably between about 15 mg/kg and 25 mg/kg body weight. These daily dose concentrations are based on isolated apocynin and isolated paeonol.

In a preferred embodiment, the preparation (or composition) is administered to a subject (e.g. human) at a concentration, per daily dose, of isolated apocynin, of between 1 mg/kg body weight and 50 mg/kg body weight, more preferably 4 to 8 mg/kg body weight. Preferably, the preparation is administered to a subject at a concentration, per daily dose, of isolated paeonol of 5 mg/kg body weight to 70 mg/kg body weight, more preferably between about 10 mg/kg and 45 mg/kg body weight, more preferably between about 15 mg/kg and 25 mg/kg body weight. More preferably, the preparation further comprises natural paeonol (e.g. *Paeonia suffruticosa*, e.g. in the form of Moutan cortex) is administered to a subject (e.g. human) at a concentration, per daily dose, of natural paeonol, of between 1 mg/kg body weight and 50 mg/kg body weight, more preferably 4 to 8 mg/kg body weight.

Preferably, the preparation (or composition) further comprises apocynin, in the natural form, and is administered to the subject at a concentration, per daily dose, of natural apocynin, of between 0.25 mg/kg and 15 m/kg, more preferably 1 to 3 mg/kg.

The doses may be increased (e.g. doubled) at the beginning of the treatment, for example for the first 1 to 3 days, as a "loading dose". Thus, as a loading dose, the preparation (or composition) may be administered to a subject (human or animal) at a concentration, per daily dose, of apocynin, of between 1 mg/kg body weight and 100 mg/kg body weight, more preferably 5 to 1[beta]mg/kg body weight. Preferably, the preparation is administered to a human or animal subject at a loading dose concentration, per daily dose, of paeonol of 5 mg/kg body weight to 140 mg/kg body weight, more preferably between about 10 mg/kg and 90 mg/kg body weight, more preferably between about 15 mg/kg and 50 mg/kg body weight. These daily dose concentrations are based on isolated apocynin and isolated paeonol. Preferably, the preparation (or composition) further comprises L-glutamine and/or Glucosamine and one or both are administered to the subject at a concentration, per daily dose, of L-glutamine and/or glucosamine of 1 mg/kg body weight to 280 mg/kg body weight, more preferably 20 mg/kg body weight to 280 mg/kg body weight, more preferably between 100 mg and 180 mg/kg body weight.

The daily dose may be provided as a single capsule, tablet or other solid or liquid form known to those skilled in the art, or may be provided in divided doses (for example 1 to 3 doses) to make up the full daily dose. The doses of apocynin and paeonol may be provided together in the capsule, tablet, etc. or the two may be provided as separate capsules or tablets for sequential administration.

According to the present invention in a further aspect, there is provided kit of parts for a preparation for treatment or prevention of inflammatory disease comprising at least one dose of apocynin; and at least one dose of paeonol. It is envisaged that the kit of parts may be provided as, for example, a blister pack containing capsules containing doses or partial doses, for example, apocynin, and separate capsules containing doses or partial doses of paeonol. The pack may be provided with instructions for sequential administration of the doses. When administered either together or separately, the compounds, should be administered such as to maintain a suitable blood level of each of the components. When administered separately, the compounds (apocynin and paeonol) should be given within 4 hours of each other, preferably within 2 hours, and most preferably substantially simultaneously.

It is preferred that the preparation is administered orally, for example, in pill or capsule form, although it is possible to use other known conventional administration techniques.

According to the present invention, in a still further aspect, there is provided a method of treatment of an inflammatory disease comprising a step of administration to a human or non-human animal subject in need thereof of a composition comprising apocynin and paeonol. According to the present invention, in a still further aspect, there is provided the use, in the manufacture of a preparation for the treatment of an inflammatory disease, of apocynin and paeonol.

Preferably the composition/preparation includes apocynin in an isolated form.

Preferably the composition/preparation includes paeonol in an isolated form.

The compositions, preparations and doses according to the invention may include other components which have anti-inflammatory properties. However, it is preferred that the paeonol and the apocynin (in isolated form and/or in natural form) represent (or lead to) substantially all of the anti-inflammatory activity of the compositions, preparations and doses.

The compositions, preparations, methods and uses may be used in combination with other (conventional) medicaments or preparations. For example, the compositions according to the invention may be used in combination with antihistamines in, for example, the treatment of an inflammatory disease such as allergic airways disease, sinusitis, etc.

The present invention will now be described in detail with reference to illustrative examples.

EXAMPLE 1

The following components are mixed in a conventional manner. This example is the formulation used in the animal (not human) examples below.

EXAMPLE 1

| | |
|---|---|
| L-glutamine | 360 g |
| Glucosamine | 360 g |
| D-Tox (Binder) (see below) | 172 g |
| Paeonol (isolated) | 90 g |
| Apocynin (isolated) | 18 g |
| | 1000 g |

The mixture was divided and prepared in a form suitable for dosing, in a capsule form for oral dose.

Dose Schedule (Animals)

In the following animal examples, Example 1 above is referred to as Example 1 and/or APPA mix. In the following studies, the mix (Example 1) was given in the feed at a rate of 5 grams twice per day per 25-kilogram body weight, or 180 milligrams and 900 milligrams per day of apocynin and paeonol (90 mg and 450 mg per dose) per 25 kilogram body weight (for dogs). For horses, the mix (Example 1) was given in the feed at a rate of 5 grams twice per day per 75-100 kilogram body weight, or 180 milligrams and 900 milligrams per day of apocynin and paeonol (90 mg and 450 mg per dose) per 75-100 kilogram body weight. The above is the usual daily dose. In the studies below, the animal was started (1-7 days) on a loading dose and once a clinical benefit is determined the dose is reduced to those noted above.

D-tox (available from Natural Animal Feeds, Monmouthshire, UK) is used as a binder. It is based on flavonoid antioxidant groups found in plants, some of which function in the water-soluble milieu and some of which function in the fat-soluble milieu. D-tox also includes a small amount of *Picrorrhiza kurroa* (apocynin in natural form).

Each 20 grams of D-tox contains (approximately):

| | |
|---|---|
| *Angelica sinensis* | 0.250 g |
| Bee pollen | 0.2 g |
| *Bulpleurum falcatum* | 0.5 g |
| *Capsicum frutescens* | 0.05 g |
| Citrus pulp | 2 g |
| *Crataegus oxycanthoides* (berries) | 1.5 g |
| *Curcuma longa* | 1.5 g |
| *Eleutherococcus senticosus* | 0.5 g |
| *Ginkgo biloba* | 1 g |
| *Glycyrrhiza glabra* | 0.5 g |
| Maitake | 0.025 g |
| Lecithin (phosphatidyl choline) | 1.8 g |
| Methionine | 0.15 g |
| N-acetyl cysteine | 0.05 g |
| *Picrorhiza kurroa* | 0.5 g |
| Riboflavin (B2) | 0.065 g |
| *Rosemarinus officinalis* | 0.75 g |
| *Schizandra chinensis* (fruit) | 1.25 g |
| *Scutellaria biacalensis* (root) | 1 g |
| *Silybum marianum* | 1.5 g |
| *Taraxacum officinale* (leaves) | 1 g |
| *Vaccinum myrtilis* | 1 g |
| Vitamin C (ascorbic acid) | 2 g |
| *Zingiber officinale* | 1 g |
| Glutamine peptide | 0.2 g |
| Total | 20.04 g |

Thus, 172 g D-Tox includes about 4.3 g *Picrorhiza kurroa* (apocynin in natural form).

Human Examples

The following preparation is used in the human examples below, and referred to as Example 1H. This mix packs into a type 'O' capsule (650 mg in total) and is taken (based on a human of body weight 60 to 80 kg) at a rate of two such capsules twice per day: am and pm. In exceptional cases (not those below) the dose may be increased at the beginning of treatment, (e.g. doubled for the first 1 to 3 days).

EXAMPLE 1H

| | |
|---|---|
| L-glutamine | 50 mg |
| Glucosamine | 50 mg |
| Moutan cortex (*Paonia suffruticosa*) | 100 mg |
| Paeonol (isolated) | 350 mg |
| Apocynin (isolated) | 100 mg |

EXAMPLE A

The subject was a 5 year old male Hungarian Vizsla with a history since 12 months old of degenerative joint disease in left and right stifle and left wrist joints. Over three years, multiple conventional "joint mixes" have been used. These have included antioxidant plant-based mixes (such as D-Tox) in conjunction with conventional NSAIDs (COX inhibitors), glucosamine, chondroitin, *Harpagophytum* spp., s-adenosyl methionine (SAMe) and MSM (methonyl sulphonyl methane). The results were satisfactory, providing an improved mobility, but the subject was not clinically sound and suffered occasional regressions. With the NSAIDs, the subject suffered many GIT-related problems, even at ¼ of the recommended doses. The Example 1 mix was introduced at the dose schedule mentioned above. Within 12 hours, the subject was clinically sound and has remained so for some 5 weeks. A further major benefit has been the absence of any GIT-related problems during treatment with Example 1.

EXAMPLE B

The subject was an 8 year old male Weimaraner with an intermittent history over two years of right shoulder lameness (which does not appear to be joint socket-related and may be ligament/tendon and muscle-related). Historically this has been difficult to treat adequately and required rest and time. A recent sudden onset that left the subject noticeably lame with difficulty in movement prompted treatment with Example 1 at the schedule mentioned above. Within 6 hours, the dog was clinically sound and has remained so.

EXAMPLE C

The subject was a 12 year old male Labrador Retriever with an extensive history of shoulder lameness. This had hitherto only been assisted by intra-articular injections of hyaluronic acid followed by intra muscular injections of NSAIDs; these severe treatments only enabled the subject to become "adequately sound". Within 24 hours of being treated with Example 1 at the schedule mentioned above the subject was as sound as he had been for several years. The subject was showing no discomfort in getting up after lying down.

As with Examples A, B and C, in the following case. studies, Example 1 ("APPA Mix") is administered according to the dose schedule set out above.

EXAMPLE D

Equine: In May 2005, this horse suffered an extremely bad accident which left his life in the balance for several months. He had severe lacerations on both his hind legs and damage to his offside hock. The vet gave him very little chance of survival due to infection and said even if he did survive, he would not be ridden again. After a major operation to clean out his hock wound and several long months of box rest and antibiotic injections, he was finally allowed outside again, although the vet still thought he would not come sound. However, at the end of September 2005, he was started on Example 1 (APPA mix) and the improvement was almost immediate. Within two months he was being ridden again (very quietly). At the beginning of March 2006, the vet gave him a full bill of health to start working 'normally' again, and sees no reason why he cannot go back to what he was doing before (advanced dressage) although we have to take it very slowly. The owner stated that: "I never before believed that a 'supplement' could really work that effectively, but you have proved me wrong! Thank you for giving me my horse back!"

EXAMPLE E

Canine: 16 yo Grand Basset Griffon Vendeen called Lizzie Hopkins. Lizzie had always coped well with exercise. Last year she walked part of south west coast path (SWCP), 7 miles daily for 10 days with no problem. Only notable medical history was off side shoulder injury at 15 months, which responded well to junior aspirin given a few days after vigorous exercise, but recently had failed to respond. Was diagnosed with onset of arthritis in Mar. 2005 5. She had begun to resist exercise in the early morning and show signs of flagging after 1.5 hrs in the afternoon. Lizzie started on APPA and, after gradual improvement, can now walk 7 miles per day with no flagging or reluctance to exercise at all.

EXAMPLE F

Equine: Hug Me Peppy, stable name Huey, is a 13 year old Quarter Horse competing in Reining classes. Huey had been on Cortaflex (glucosamine-based mix) for two years, with good results, but recently changed to APPA. Huey's owner, says "the results are incredible, he used to drag his back legs a bit but watching him move now you'd think it was a different horse. Huey is now much better to ride and has a real spring in his step. It's great to think he still has years ahead of him. Thank you for developing such a wonderful supplement"

EXAMPLE G

Equine: William is an 18.3 hh, 11 yr old TB×ID gelding, who has had numerous leg injuries over the past four years which lead to stiffness, joint clicking and a haematoma on his hock. The vet recommended using Adequan (intra-articular poly-sulphated-aminoglycans) but his owner decided to put him on APPA. William now has no clicking in his joints and the haematoma on his hock has reduced considerably.

EXAMPLE H

Equine: Dublin Dice is a two year old TB racehorse who showed joint swelling following a race. An X-ray was done which showed no serious problem, but the horse was rested from work. Dublin was put on APPA and an improvement was seen within a week. He is now sound and back in full work and due to run again.

EXAMPLE I

Canine: 6 y.o. male Hungarian Viszla with a history since 12 months old of degenerative joint disease in L and R stifle and L wrist joints. Over three years multiple *joint mixes* have been used. These have included antioxidant plant-based mixes (D-Tox) mixes in conjunction with NSAIDs (COX inhibitors), glucosamine, chondroitin, *Harpagophytum* spp., s-adenosyl methionine (SAMe) and MSM (methonyl sulphonyl methane). The results were satisfactory providing an improved mobility, but not clinically sound, with occasional regressions. With the NSAIDs there many GIT-related problems, even at ¼ recommended doses. APPA mix (Example 1) was introduced at the above schedule—within 12 hours he was clinically sound and has remained so now for some 18 months. Another major benefit has been the absence of any GIT-related problems.

EXAMPLE J

Canine: 9 y.o. male Weimaraner with an intermittent history over two years of R shoulder lameness that does not appear to be joint socket related and may be ligament/tendon and muscle related. Historically, this has been difficult to treat adequately and required rest and time. A recent sudden onset that left him noticeably lame with difficulty in movement prompted administration of the APPA mix. Within 6 hours he was clinically sound (the lameness had gone) and has remained so for 18 months.

EXAMPLE K

Cainine: 12 y.o. male Labrador Retriever with an extensive history of shoulder lameness that has only been assisted by intra-articular injections of hyaluronic acid followed by intramuscular injections of NSAIDs that enabled him to become "adequately sound". Within 24 hours of being supplemented with the APPA mix he was as sound as he had been for several years. He also was showing no discomfort in getting up after lying down.

EXAMPLE L

Canine: 9 y.o. male Weimaraner with a history of left fore superficial flexor strain accompanied by swelling around the injured region, causing lameness and inability to exercise. Conservative treatment required rest and relative inactivity—always difficult to achieve in canines, especially so in the sporting breeds. APPA Mix has substantially resolved this problem, becoming sound within 24 hours, but can be re-aggravated when the injured tendon is provoked by very strenuous exercise. APPA Mix resolved the clinical signs.

EXAMPLE M

Human: 40 y.o. female with a history (since the early 1990s) of degenerative knee joint problems initially caused by meniscus tears incurred while skiing. Over the ensuing years this degenerative joint disease has steadily progressed until the stage where it was not longer possible to go up stairs without pain and activities such as those that specifically involved the knee joints, such as kneeling, were no longer possible. Consultations and treatment regimes with orthopaedic specialists and which involved, inter alia, intraarticular injections (corticosteroids and/or hyaluronic acid) initially provided some relief but more recently were no longer doing so. A course of the Example 1H was started. Within ten days the patient observed a diminution in swelling and some freedom of movement. By 28 days the patient reported full mobility—with minimal discomfort—and reported that she was now able to walk freely and without discomfort. Undertakings such as walking up stairs and kneeling were now possible without discomfort.

EXAMPLE N

Human: 35 y.o. female with a long-term history of flexural discomfort of the P5 interphalangeal joints of the left hand. This clinical problem had left the patient unable to flex her finger and thus noticeably impeded her sporting activities such as tennis. A course of Example IH was started. Within ten days the patient observed a diminution in discomfort and an increased freedom of movement. By 28 days, the patient reported full mobility and reported that she was now able to move the interphalangeal joints involved freely and without discomfort.

EXAMPLE O

Human: 82 y.o female with a history of R. total hip (coxofemoral joint) replacement and starting to observe increasing pain/discomfort in the L. hip joint. A course of the Example 1H was started. Within ten days, the patient observed a marked decrease in discomfort and an increased freedom of painless movement. By 21 days, the patient reported full mobility of the L hip joint without further painful episodes.

EXAMPLE P

Human: 58 yo. male with a 45 year history of occasional acute onset lumbar spasms that gave continuous unremitting debilitating pain. In the past, whatever pain relieving-medication had been prescribed was not helpful. This problem could only ever be alleviated by chiropractic/osteopathic manipulative procedures. After an onset of lumbar spasms and radiating pain down the R. leg possibly caused by recent excessive manual labour and which involved lifting multiple heavy weights, however, a clinical consultation with a chiropracticioner was not possible for several days. A course of Example 1H was instituted. Within 15 hours, the patient observed a marked and noticeable diminution in lumbar discomfort and an increased ability to perform pain-free activity. By 24 hours, the patient reported full mobility and pain-free movement but said he would not feel completely at-ease happy until he had visited his chiropractitioner.

EXAMPLE Q

Human: 32 y.o. female with a history of L. popliteal bursitis with diminished flexural ability, thus restricting athletic activity. The patient had been undergoing long-term physiotherapy without much success. A course of Example 1H was started. Within ten days, the patient observed a diminution in discomfort and an increased freedom of movement. By 28 days, the patient reported a much greater freedom of movement, with the pain-free flexural ability much closer to that normally expected for that joint.

EXAMPLE R

Canine: 7 y.o. male Labrador with a history of Grade 111 bilateral hip dysplasia which significantly reduced his ability to move freely. After some years being supplemented with a chondroprotective mix of chondroitin and glucosamine, which provided some increased freedom of movement, a course of the APPA mix was instituted as an alternative to determine if it could provide an improved pain-free mobility. Within ten days, the owner observed a diminution in discomfort and an apparent increased freedom of movement in comparison to the chondroprotective mix of chondroitin and glucosamine. By 21 days, the patient was reported to have close to full mobility and it was further reported that no further clinical signs of pain were observed when getting up from lying down and/or going up stairs and/or jumping and/or exercising.

EXAMPLE S

Canine: 12 y.o. female recently thought to be Cushinoid, however, the steroid stimulation test was negative. Over the past years she had become lethargic and now moved with a discomfort thought to be osteoarthritic in origin. A course of APPA Mix was instituted and her owner (a human MD) reports that she now has become noticeably more active, playful, seems happier and eats very well with less fussiness over the menu. Her movement is, however, somewhat less lame in nature but she has walked like that for some time and uses the rabbit hop as a result of joint fusion rather than osteoarthritis. Her owners states: " . . . a remarkable difference."

EXAMPLE T

Human: 24 y.o. male with a history of an acute trauma which involved a low fracture of the tibia and fibula (a Potts-like fracture not only involving the medial malleolus but also fracturing the calcaneus). The patient has undergone multiple surgical procedures in order to regain some mobility. However, the patient experienced continued pain, swelling and only partial mobility. A course of Example IH was started. Within 21 days the patient reported a diminution in swelling and increased pain-free movement. By 45 days the patient reported an improved mobility—with less discomfort—but still not normal. However a noticeable greater freedom of pain-free movement was now for the first time possible since the accident.

EXAMPLE U

Equine: 8 y.o Standardbred Mare diagnosed with Degenerative Joint Disease of the R. interphalangeal P1/P2 joint presenting with intermittent lameness. A course of the APPA mix was started, as set out in Example 1 above. Within five days the horse became clinically sound and exhibited no further clinical signs relating to the osteoarthritis. However, after eight weeks veterinary advice was sought as the horse had again become lame in the R. foreleg. On consultation, it was determined that the APPA Mix had been finished and that the owner last supplemented the horse with APPA Mix some 10 days previously. Again the APPA Mix was instituted into the therapeutic protocol and, within 24 hours, the horse was much improved returning to full soundness over the following days and has remained so with ongoing supplementation of the APPA Mix.

EXAMPLE V

Equine: 7 y.o. Spanishbred Stallion used for long-distance races presented with a long term history of intermittent lameness. On veterinary examination, the horse was diagnosed with Degenerative Joint Disease (osteoarthritis) of the R and L hock joints (tarsal-metatarsal joints) with the R. showing greater discomfort than the L. A course of APPA Mix (Example 1) was started with the horse showing a gradual improvement towards soundness over the next few days and returning to full soundness by day 10. Since that time, the horse has competed successfully, placing 2nd in the National Championships—in international long distance riding events (50+ kilometers)

EXAMPLE W

Human: 21 y.o male with chronic interphalangeal joint laxity, swelling and discomfort—possibly due to torn/damaged tendon insertion. A course of Example IH was advised. After 5 days, the patient reported a much improved joint and noticed a reduction in the swelling. Within 21 days, the patient reported—confirmed by clinical examination—normal joint activity and function. Since that time, the patient reports no further discomfort from this problem.

EXAMPLE X

Human: 53 y.o. female presented with inflamed and painful sinus cavities, likely to be the result of seasonal allergies. Previously the patient had used antihistamine medications in order to obtain relief. A course of Example 1H was suggested as an alternative to antihistamines. The patient reported a noticeable symptomatic improvement after some 3-4 hours. However the problem had not complexly resolved and an antihistamine was also taken. The patient then reported a return to normal. The patient additionally noted that the combination of the antihistamine and the Example 1H helped resolve this seasonal allergic sinus problem more completely and more rapidly than using antihistamine medication alone. Since that time, the patient—as a first choice option—has used this combination therapy whenever there is a reoccurrence of the seasonal allergic problem.

COMPARISON EXAMPLE 1

The subject of Example A had previously been treated by D-tox, which includes apocynin (in the natural form). There was some improvement of the subject's condition but other medication was still needed.

The applicant has noted that the effect of the combination of paeonol and apocynin together is rather better than would have been expected from studies using either of these alone. In other words, it appears there is a synergistic effect when paeonol and apocynin are used together. Indeed, when used on their own paeonol and apocynin did not show anti-inflammatory and/or analgesic activity that could be clinically observed.

The plant extracts and other reagents used in the formulations are readily available to the skilled man. For example, moutan cortex and paeonol are available from e.g. bulk suppliers of herb and plant extracts such as XUANCHENG BAICAO PLANTS INDUSTRY & TRADE CO., LTD of China. L-glutamine and glucosamine are readily available in bulk from quality raw materials suppliers but can also be brought from shops/chemists. Apocynin is available from Sigma Tau (a.k.a. Aldritch which is their commercial arm) fine chemical suppliers of Germany.

The invention claimed is:

1. A composition comprising apocynin and paeonol, wherein the weight ratio of apocynin to paeonol is between about 1 to 1 and about 1 to 10.

2. A composition according to claim 1 further comprising L-glutamine.

3. A composition according to claim 2, additionally comprising a filler.

4. A composition according to claim 1 further comprising glucosamine.

5. A pharmaceutical or veterinary preparation comprising a composition according to claim 1.

6. A pharmaceutical or veterinary preparation according to claim 5 for the treatment of inflammatory disease.

7. A composition comprising L-glutamine; glucosamine; a binder; paeonol; and apocynin in the ratio in parts by weight of 360:360:172:90:18.

8. A composition comprising L-glutamine; glucosamine; a binder; paeonol; and apocynin in the ratio in parts by weight of 360:360:172:90:18, wherein the binder comprises apocynin in the natural form, at an amount in parts by weight of the total composition, of between about 4 and 4.6.

9. A composition according to claim 1, wherein the weight ratio of paeonol to apocynin is 3.5 to 1.

10. A composition according to claim 1, wherein the weight ratio of apocynin to paeonol is between about 1 to 1 and about 1 to 6.

11. A composition according to claim 10, wherein the weight ratio of apocynin to paeonol is between about 1 to 2 and about 1 to 6.

12. A composition according to claim 1, wherein the weight ratio of apocynin to paenol is between about 1 to 2 and about 1 to 10.

* * * * *